United States Patent [19]

Sano et al.

[11] Patent Number: 5,511,551
[45] Date of Patent: Apr. 30, 1996

[54] CUFF FOR BLOOD PRESSURE METER

[75] Inventors: Yoshihiko Sano; Toshiyuki Kobayashi, both of Kyoto; Tsutomu Teramoto, Nara; Kouta Fukumura, Kyoto, all of Japan

[73] Assignee: Omron Corporation, Najaokakyo, Japan

[21] Appl. No.: 213,425

[22] Filed: Mar. 15, 1994

[51] Int. Cl.$^6$ ...................................................... A61B 5/00
[52] U.S. Cl. ............................................ 128/686; 606/202
[58] Field of Search .................... 128/686; 606/201–207; 601/12

[56] References Cited

U.S. PATENT DOCUMENTS

| | | | |
|---|---|---|---|
| 2,452,799 | 11/1948 | Speaker et al. | 128/2.1 |
| 2,678,040 | 5/1954 | Poole et al. | 128/205 |
| 4,331,155 | 5/1982 | Sacks | 128/686 |
| 4,667,672 | 5/1987 | Romanowski | 128/686 |
| 4,771,790 | 9/1988 | Yamasawa et al. | 128/686 |
| 4,850,369 | 7/1989 | Yamasawa | 178/686 |
| 4,860,761 | 8/1989 | Yamasawa et al. | 128/686 |
| 4,862,895 | 9/1989 | Yamasawa et al. | 128/680 |
| 5,086,514 | 2/1992 | Ross | 2/DIG. 3 |
| 5,121,964 | 6/1992 | Holtsch | 606/203 |
| 5,312,431 | 5/1994 | McEwen | 606/202 |

FOREIGN PATENT DOCUMENTS

| | | |
|---|---|---|
| 3612532 | 10/1986 | Germany . |
| WO8300426 | 2/1983 | WIPO . |

OTHER PUBLICATIONS

European Search Report dated Jul. 20, 1994.

*Primary Examiner*—Angela D. Sykes
*Assistant Examiner*—Robert L. Nassei, Jr.
*Attorney, Agent, or Firm*—Fish & Richardson

[57] ABSTRACT

A cuff for a blood pressure meter includes material that does not stretch and in which the length of the surface in contact with the finger does not vary when the cuff is filled with compressed air, regardless of the diameter of the finger. Because the internal pressure in the cuff closely approximates the blood pressure of the finger, the device is accurate. Compressed air is pumped into chambers formed by a basic structure and containment walls. Folded portions which are provided on the containment walls cause surfaces of the containment walls which contact the object to be measured to remain parallel to protruding bodies located on the basic structure as they are displaced by inflation of the chambers.

15 Claims, 9 Drawing Sheets

CUFF FOR BLOOD PRESSURE METER

FIELD OF THE INVENTION

This invention concerns a cuff used to measure blood pressure. More specifically, it concerns a cuff for a blood pressure meter which measures blood pressure when applied to a finger.

BACKGROUND OF THE INVENTION

FIG. 16 is a perspective view of a conventional finger blood pressure meter. FIG. 17 is a cross-sectional view of a conventional blood pressure meter finger cuff. Several types of designs of finger cuffs are currently available.

The finger cuff shown in FIG. 17 has a wrapper constituting a sheet (or membrane) made of rubber or a soft plastic which is folded over on itself. Chamber 501, which contains compressed air, is formed by welding or bonding the ends of this sheet. Generally, the outside of chamber 501 has strips of cloth around its top and bottom ends which cause it to assume the shape of a cylinder when inflated. Cylindrical cuff or chamber 501, is enclosed within cylindrical case 500.

To measure a patient's blood pressure, the patient inserts his finger into the cylindrical cuff 501. When chamber 501 is filled with compressed air via the air tube connected to it, it expands like a balloon, adhering to and pressing against the finger. The blood pressure is measured by obstructing the flow of blood in the artery of the finger.

As seen in FIG. 16, the finger 400 inserted in the cylindrical cuff does not touch anything outside of the cuff nor does it rest on a fixed member or support. A patient often bends his finger, thus not relaxing the finger for an accurate measurement because there is no support on which the patient can rest his finger. As a result of the tension in the finger, inaccurate blood pressure measurements are taken.

In the conventional blood pressure finger cuff described above, the range of finger sizes to which the cuff can be applied properly is limited. If a person's finger size happens to match the finger cuff size, pressure would be applied to the finger as the cylindrical cuff or chamber is filled with compressed air. If the finger to be measured does not match the finger cuff size, but is, for example, thinner than the finger size optimal for the finger cuff, the chamber is stretched and deformed by the pressure applied by the compressed air before the cuff is expanded enough to cause its surface to press against the finger. The tension caused by the deformation of the chamber affects the pressure inside the finger cuff, and the pressure applied to the finger is reduced. If pressurization were continued while the chamber was deformed, the sum of the pressure against the finger and the pressure required to expand the cuff would equal the internal pressure of the cuff. The result would be that the internal pressure in the cuff would not correspond to the blood pressure value. Since this type of chamber deforms when it stretches, the insertion of a thin finger in the cuff causes the midline cross-section to expand like a balloon, while the two ends of the chamber, along the path of insertion, become round. Thus, both the shape of the cylindrical cuff and its length when pressed against a finger vary with the diameter of the finger. This variation leads to measurement errors.

An example of this can be seen in FIG. 17. When chamber 501 expands like a balloon, the length of the surface in contact with the finger, which was originally $l_1$, is reduced to $l_2$.

Another disadvantage of this type of cuff is that the material of the air containment wall or chamber is limited to materials which can stretch, yet are highly stable, i.e., materials capable of substantial elastic deformation.

As seen in FIG. 18, a conventional finger cuff has many parts to assemble, in this case, five pieces. In this conventional finger cuff, a long, flat air chamber 590 is rolled into a cylinder 591a, 591b, both ends of which are taped on both surfaces to form a permanent tube then sealed by end pieces 592, 593. The task of winding the cuff into a cylinder is extremely complicated, and thus, assembling the cuff is difficult.

SUMMARY OF THE INVENTION

This invention provides a cuff for a blood pressure meter which solves the problems described above. Such a cuff is made of a material which does not stretch regardless of the diameter of the object to be measured (a finger, for example) and the length of the portion of cuff in contact with the object to be measured does not vary. As a result, the pressure within the cuff closely approximates the blood pressure of the object so that an accurate measurement is made.

A cuff for a blood pressure meter of this invention is described below.

A cuff for a blood pressure meter according to this invention includes a belt having a plurality of protruding bodies disposed thereon and an air bag or chamber disposed over the protruding bodies on the belt for receiving compressed air. The cuff further includes at least one containment wall disposed on the belt, forming with the belt an air bag or chamber for receiving compressed air, and at least a pair of folded portions on each of the containment walls which cause the surface portions of the containment walls, the portions which make contact with a patient's finger, to remain parallel to the protruding bodies when the volume enclosed by the belt, protruding bodies, and containment walls is filled with compressed air.

This cuff has a number of protruding bodies which protrude inwardly from the inner surface of the belt, when the belt is formed into a cuff. The belt or basic structure has a cylindrical shape. The containment walls for compressed air, which are formed from a thin sheet, are located on the surface of the basic structure, over the protruding bodies. The edges of the containment walls are connected to the belt. Compressed air is pumped into a chamber located between the belt and the protruding bodies thereon, and the containment walls.

The folding portions are located at either end of the containment walls at right angles to the path along which the finger is inserted. Ordinarily, the surfaces of the containment walls which contact the object to be measured touch the level horizontal surfaces of the protruding bodies. To measure a patient's blood pressure, one inserts the object to be measured (i.e., a finger), and compressed air is pumped into the chamber. The portions on either end of the containment walls which are folded toward the periphery rise up (i.e., the portions move toward the interior of the cuff), and as these portions move, the surfaces which come in contact with the finger remain parallel with the flat surfaces of the protruding bodies. The folded portions assist the containment walls to maintain contact with the finger. As the compressed air fills the chamber, the containment walls are pushed inward toward the finger. These walls do not stretch when the chamber is filled with compressed air. Even when the object to be measured (i.e., a finger) is thinner than the cuff, the internal pressure in the cuff is not increased by the force of expansion. The length of the surface in contact with the finger does not vary with the diameter of the finger, and the blood pressure can be measured with accuracy.

In another aspect of this invention, a cuff for a blood pressure meter includes a belt having containment walls for compressed air furnished to the structure, a locking device on one end, and a lock on the other end. When the locking device is engaged with the lock, the belt assumes a cylindrical form. In this cuff for a blood pressure meter, a projection which is the locking device is located on one end of the belt, while a slit which is the lock into which the projection engages is located on the other end of the belt. This long, flat cuff is rolled into a cylinder. The cylindrical shape is maintained by fitting the projection into the slit. Thus, assembly of the cuff is extremely simple.

This cuff for a blood pressure meter can further include a support, or a finger bed, located at one end of the blood pressure meter finger cuff on which the patient can rest his finger. The patient can then relax his finger in order to obtain a more accurate blood pressure measurement.

The cuff according to this invention has many advantages:

(1) The upward movement of the folded portions prevents the material of the containment walls from stretching and deforming.

(2) The surface areas of the containment walls which contact the finger do not vary with the thickness of the finger.

(3) The shape of the contacting surface does not vary due to the force of expansion.

(4) Additionally, because the folded portions move, an expansion force does not increase the internal pressure in the cuff. Thus, the internal pressure in the cuff closely approximates the blood pressure in the finger.

(5) When the cuff is pressurized, its cross-section will not assume the shape of a balloon, as in conventional cuffs.

(6) Since this design requires less air to achieve a given pressure, the signal-to-noise ratio of the pulsewave which is detected will be larger.

(7) Because the material of the containment wall does not need to stretch, it need not be limited to only those materials which can withstand substantial elastic deformation. Rather, a wide range of materials can be chosen.

(8) A cylindrical cuff is easily formed by engaging the locking device and the lock.

(9) The finger bed on the cuff ensures that the patient's finger is relaxed in order for an accurate measurement to be made.

(10) The cuff comprises three segments which allow for easy assembly and shorter assembly time, as compared with conventional finger cuffs.

DETAILED DESCRIPTION OF THE INVENTION

Figure 1:
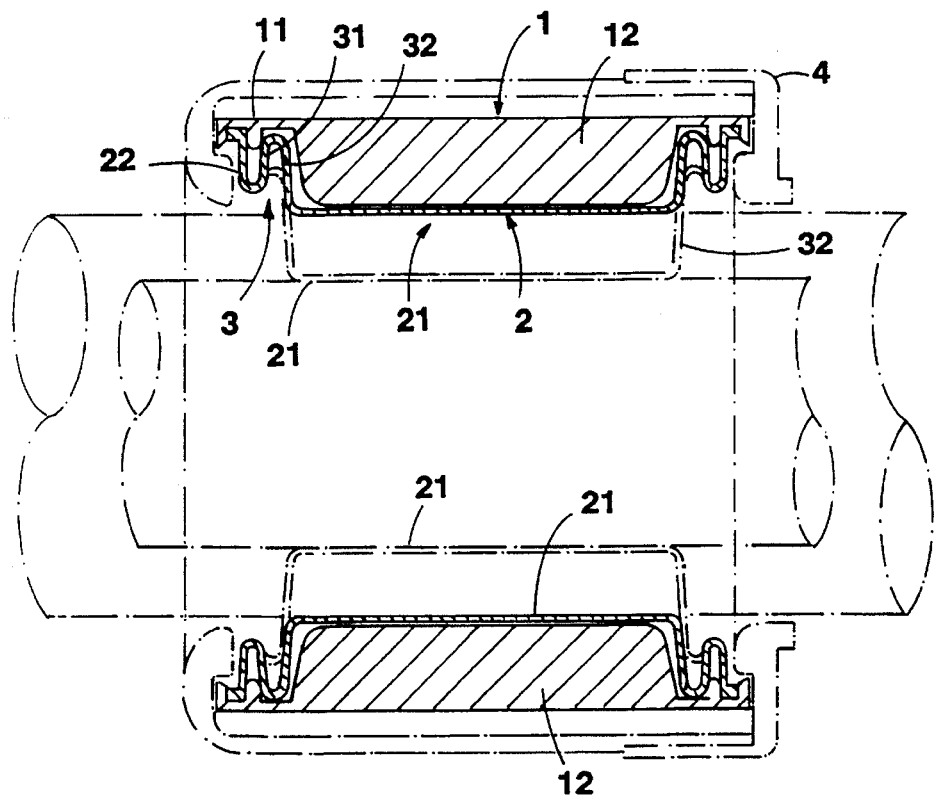
FIG. 1 is a cross-sectional view of a first embodiment of a cuff for a blood pressure meter.

FIG. 1 is a cross-sectional view of a first embodiment of the cuff for a blood pressure meter.

The cuff for a blood pressure meter shown in this first embodiment is a finger cuff. This finger cuff comprises a belt or basic structure 1; at least one containment wall 2 located on belt 1; at least one chamber 6 for compressed air; and folded portions 3 located on containment walls 2. When compressed air is pumped into the chambers 6 formed by belt 1 and containment walls 2, the surfaces 21 of containment walls 2, which contact the finger are forced to remain parallel to the bases of the protruding bodies 12 by folded portions 3.

Figure 2:
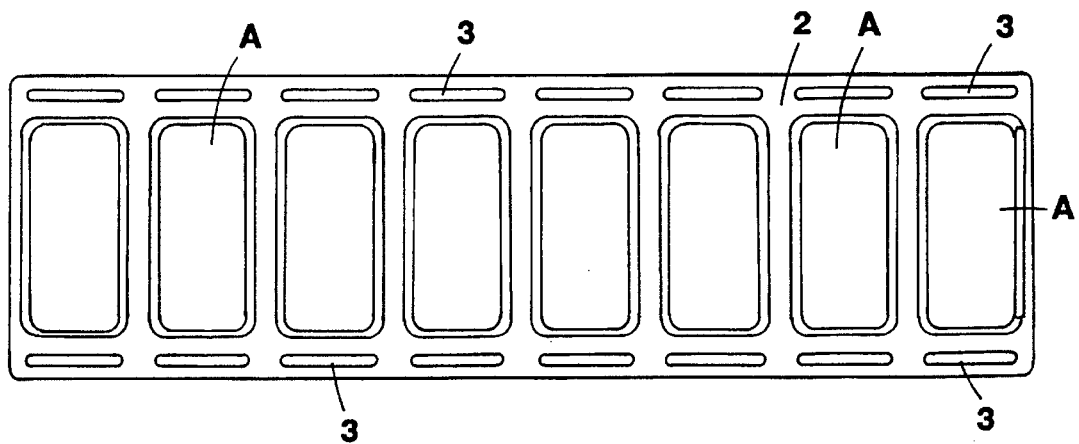
FIG. 2 is a plan view of the first embodiment of a cuff for a blood pressure meter.
Figure 3:
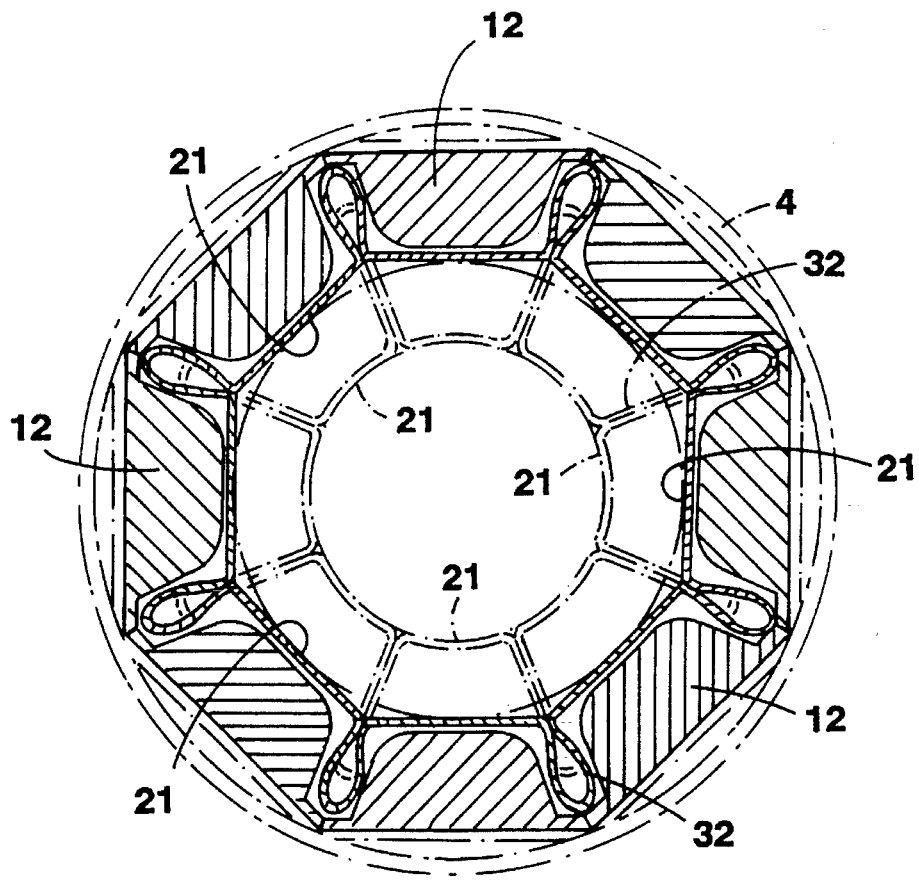
FIG. 3 is a cross-sectional view of the first embodiment of a cuff for a blood pressure meter.

As can be seen in FIGS. 1–3, belt 1 includes thin panel 11 and a number of protruding bodies 12. Protruding bodies 12 are formed on the inner surface of panel 11 and extend toward the interior of the cuff. In this embodiment, eight protruding bodies 12 are provided (see FIGS. 2 and 3) so that each protruding body has a flat upper surface to the outside of the cuff. Containment walls 2 are formed by a long strip of material in the form of a sheet or membrane of specified length and width. The containment walls are attached to belt 1 on one side. As shown in FIG. 1, side fitting segments 22 are located on either end of each containment wall 2. Side fitting segments 22 are mounted to basic structure 1 at the beginning and the end of the path along which the finger is inserted. With this structure, contacting surfaces 21 of containment walls 2 contact the upper surfaces of protruding bodies 12, which are arrayed next to each other. Basic structure 1 to which containment wall 2 is attached is rolled into a cylinder, as shown in FIG. 3, and enclosed within cylindrical outer case 4.

As shown in FIG. 1, the folded portions 3 are located at either end of the containment walls at right angles to the path along which the finger is inserted. Each folded portion 3 includes side fitting segment 22; outer curved segment 31, which starts at the tip of side fitting segment 22, is attached to basic structure 1 and folded until segment 31 is parallel to side fitting segment 22; and an inner curved segment 32, which starts at the tip of outer curved segment 31, is folded until inner curved segment 32 is parallel to outer curved segment 31. Compressed air is pumped into the chambers 6 located between containment walls 2 with folded portions 3 and basic structure 1.

In such a cuff for a blood pressure meter, folded portions 3 are provided at right angles to the path along which the finger is inserted at both the beginning and the end of the path. When a finger is inserted and compressed air is pumped into the chamber 6 formed by basic structure 1 and containment walls 2, folded portions 3, which are normally oriented toward the periphery on either end of each containment wall 2, rise up (i.e., they move toward the interior of the cuff). In other words, as shown in FIGS. 1 and 3, outer curved segment 31 and inner curved segment 32 extend in a straight line from side fitting segment 22. Contacting portions 21 of the containment walls 2, which normally contact the flat surfaces of the protruding bodies 12, remain parallel with the flat surfaces as they are pushed inwardly when the chamber 6 inflates, and the finger is compressed. Containment walls 2, which are formed from a thin sheet of material, are not stretched during inflation of the cuff.

Even when the object to be measured (i.e., the finger) is thin, the internal pressure in the cuff is not increased by the force of expansion. The length of the surface in contact with the finger does not vary with the diameter of the finger, and the blood pressure can be measured with acceptable accuracy.

In this embodiment, eight protruding bodies 12 are provided on the inner surface of basic structure 1. However, any number of protruding bodies 12 may be used.

Figure 4:
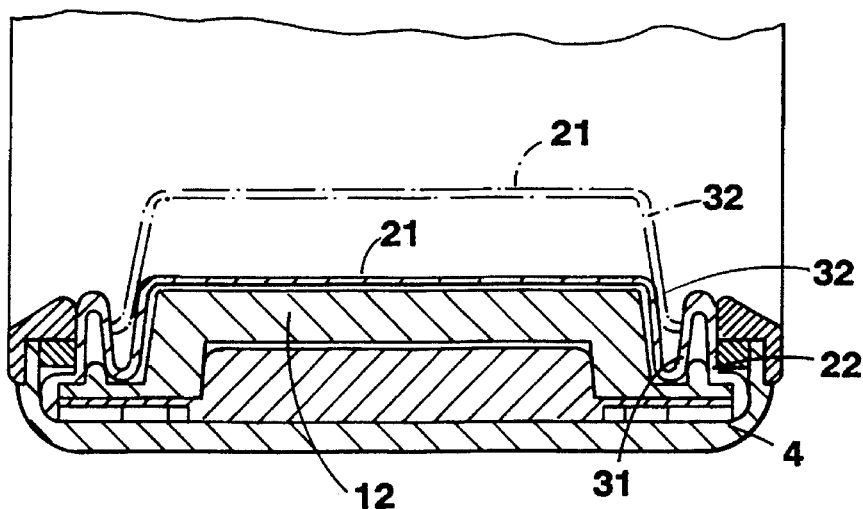
FIG. 4 is a cross-sectional view showing the components of a second embodiment of the cuff for a blood pressure meter.

FIG. 4 is a partial cross-sectional view of a second embodiment of the cuff for a blood pressure meter. In this embodiment, side fitting segments 22, which are connected to folded portions 3, are thicker than the folded portions. Outer curved segments 31 and inner curved segments 32, which are formed by folding the material back on outer curved segments 31, have the same width as contacting surfaces 21, while side fitting segments 22 are wider.

In this embodiment, side fitting segments 22, which are connected to folded portions 3, are made of a hard material. When compressed air is pumped into the chambers 6 located between basic structure 1 and containment walls 2, folded portions 3 readily move inward toward the object to be measured while side fitting segments 22 are prevented from expanding or bending toward the edges of the cuff as they are pushed by the compressed air. This helps ensure that contacting surfaces 21 can only move upward i.e., toward the interior of the cuff.

Figure 5:
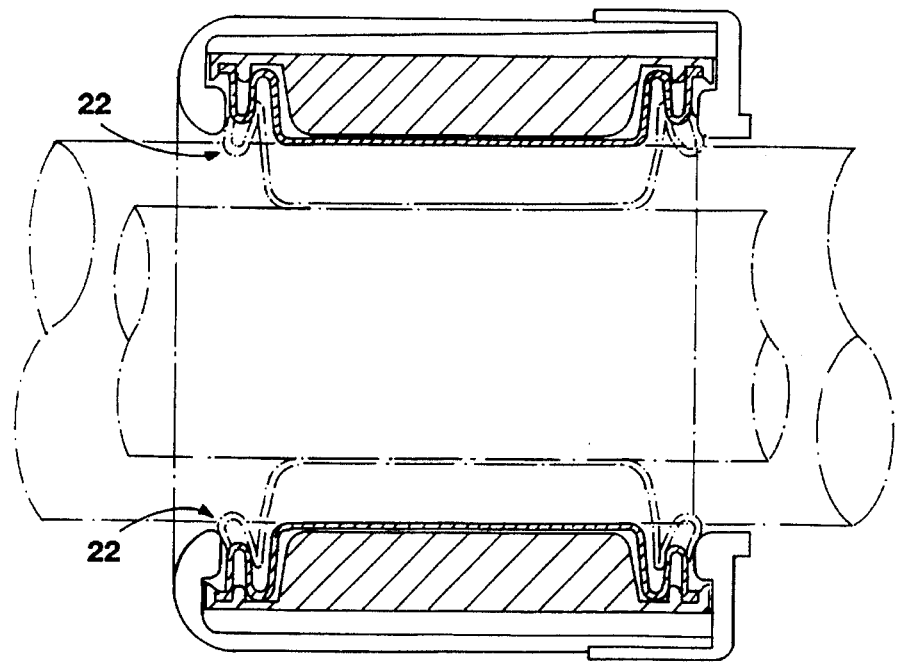
FIG. 5 is a cross-sectional view showing the folded portion bent out from the edge of the outer case.

FIG. 5 shows that the side fitting segments 22 may expand or bend toward the edges of the cuff as they are pushed by the compressed air, particularly when the side fitting segments 22 rise up over the edge of the cuff. When the measurement steps start in this case, the air pressure in the cuff is gradually lowered. Then, the expanding or bending portion of the side fitting segment 22 recovers to its original shape once the air pressure falls under a certain level. This causes a shock in the inner pressure of the cuff, and often leads to a mistaken measurement of the blood pressure.

Figure 6:
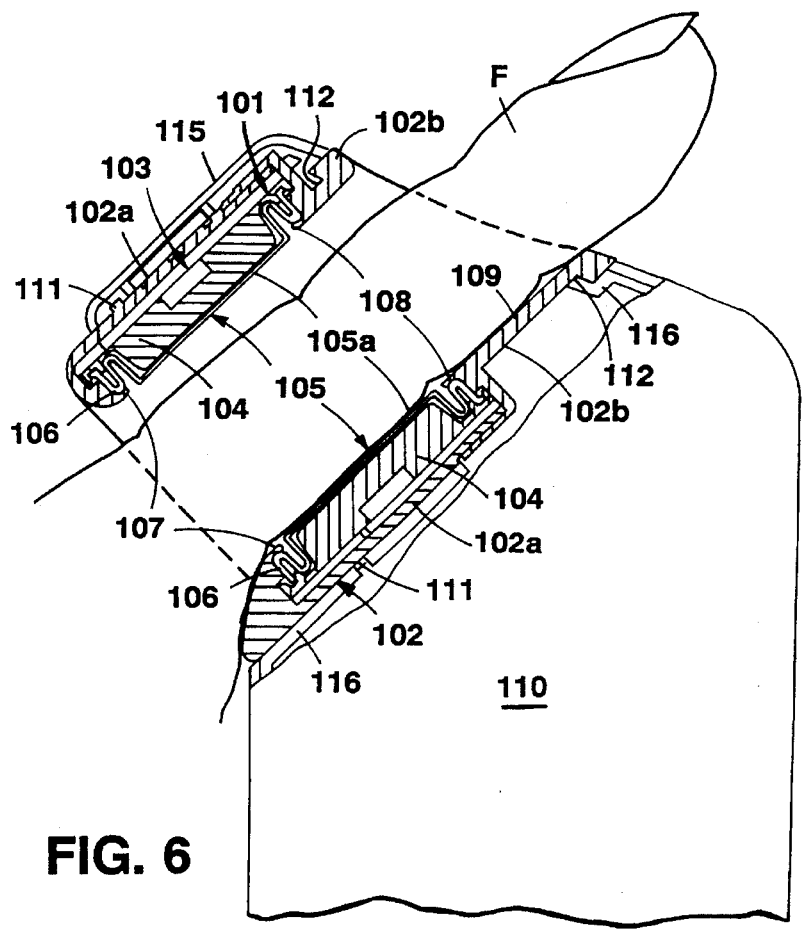
FIG. 6 is a cross-sectional view showing a guard on the folded portion which is a modification of the first and second embodiments, and a finger bed at one end of the cuff which is described in a sixth embodiment.

FIG. 6 shows another modification of the cuff. The folding guards 107, 108 located over the side fitting segments 22 are provided to overcome the above problem. The folding guards 107, 108 prevent the side fitting segments 22 from bending toward the edges of the cuff, so that the inner curved segment 32 and the outer curved segment 31 smoothly move only when inflated without bending the side fitting segments 22 to the sides.

FIG. 6 also shows projection 111 around the cuff holder segment 102a and a concave space 112 around cuff holder segment 102b. Cuff holder 102 comprises cuff holder segments 102a, 102b. When cuff holder 102 is inserted into the main unit 110, it is easily positioned by engaging projection 111 and the concave spaces 112 with the corresponding engagement structures of main unit 110. This configuration reduces the assembly time for the cuff.

Figure 7:
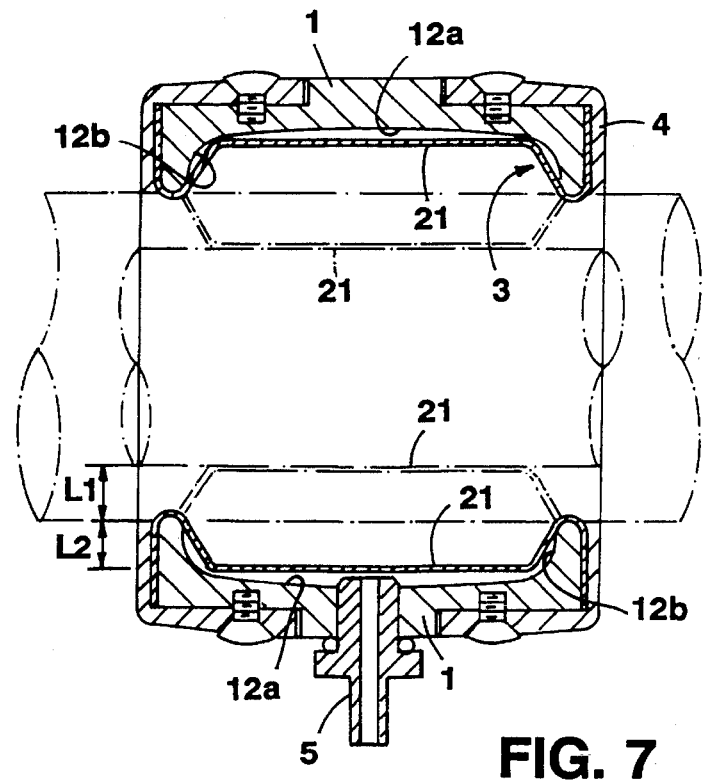
FIG. 7 is a cross-sectional view of a third embodiment of the cuff for a blood pressure meter.

FIG. 7 shows a cross-sectional view of a third embodiment of the cuff for a blood pressure meter. In this cuff for a blood pressure meter, belt 1 is cylindrical, and the inner surface of its body has a number of concave portions 12a facing the interior of the cuff. Containment walls 2, which are formed from a sheet or membrane of material, are attached to basic structure 1 when side fitting segments 22 are sandwiched between cylindrical case 4 and the exterior of basic structure 1. With this design, contacting surfaces 21 of containment walls 2 are positioned so that they contact the flat bottoms of concave portions 12a in the body. Folded portions 3, which are connected to side fitting segments 22, conform to the shape of rim portions 12b, which are the curved portions on either side of the flat bottom of concave portions 12a. During inflation, folded portions 3 are folded toward the interior of the cuff.

In a cuff according to this embodiment, when compressed air is pumped via connector tube 5 into the chambers 6 formed by basic structure 1 and containment walls 2, folded portions 3, which are angled toward the interior of the cuff, rise toward the interior. Flat contacting surfaces 21 remain flat as they are inflated. In other words, surfaces 21 expand into the interior of the cuff. This design prevents containment walls 2 from stretching and deforming when the chamber 6 is filled with compressed air. As is shown in FIG. 7, since the length $L_2$ of the folded portions is equal to the maximum displacement $L_1$, an expansion force is not generated when the finger inserted in the cuff is thinner than average.

Figure 8:
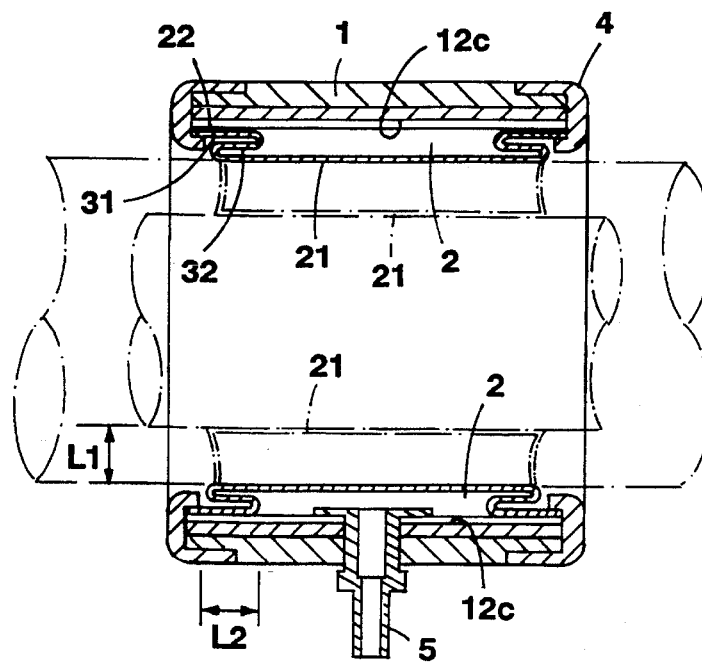
FIG. 8 is a cross-sectional view of a fourth embodiment of the cuff for a blood pressure meter.

FIG. 8 is a cross-sectional view of a fourth embodiment of the cuff for a blood pressure meter. In this cuff for a blood pressure meter, belt 1 is flat. Flat protruding bodies 12c are formed on and integrally with the flat surfaces of structure 1. Belt 1, including flat protruding bodies 12c, is rolled into a cylinder and fitted into cylindrical case 4. Containment walls 2 form sac-like chambers 6 with the belt parallel to the path along which the finger is inserted. Folded portions 3 are found at both ends of this path. Folded portions 3 comprise outer curved segments 31 and inner curved segments 32, which are connected to outer curved segments 31. The outer curved segments 31 and the inner curved segments 32 overlap each other perpendicular to the path of the finger, i.e., toward the interior of the cuff. In this design, the rear surfaces of containment walls 2, which are connected to folded portions 3, contact with flat protruding bodies 12c. Contacting surfaces 21, which are also connected to folded portions 3, are parallel to flat protruding bodies 12c.

In a cuff for a blood pressure meter according to this embodiment, when compressed air is pumped into the chambers 6 formed by basic structure 1 and containment walls 2 via connector tube 5, folded portions 3, which are folded over toward the interior of the cuff parallel to the path of the finger, rise up. In other words, outer curved segments 31 and inner curved segments 32 assume the form of straight lines extending toward the interior of the cuff, and contacting surfaces 21 remain horizontal as they are pushed upward. Thus, containment walls 2 are not stretched and deformed. As is shown in FIG. 8, the maximum displacement $L_1$ when the surface of the cuff is not experiencing expansion force is equal to $2 \times L_2$. Thus, the internal pressure in the cuff will not increase because of an expansion force when the finger inserted in the cuff is thinner than average.

Figure 9:
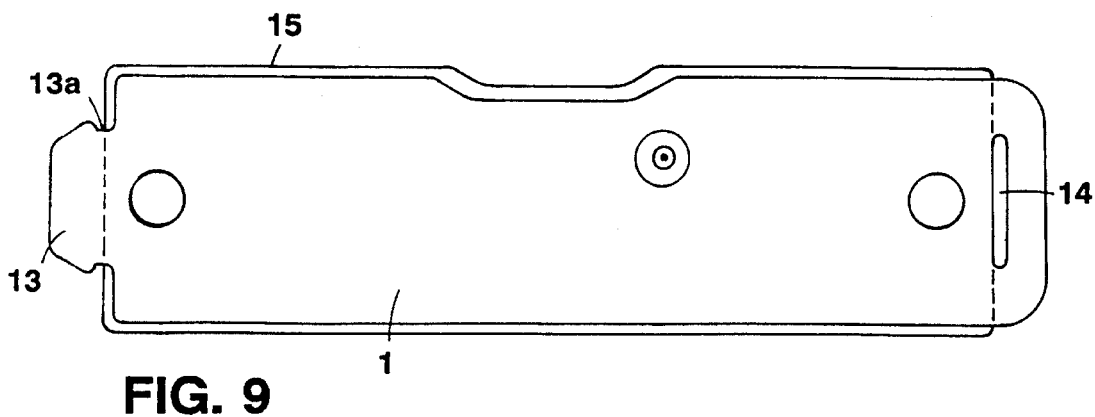
FIG. 9 is a plan view of a fifth embodiment of the cuff for a blood pressure meter.
Figure 10:
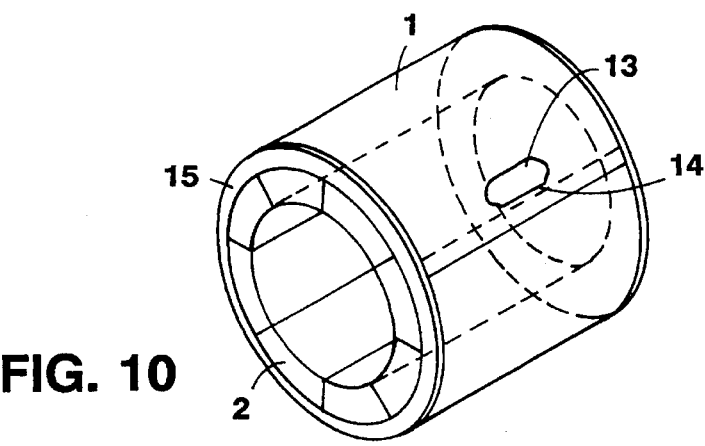
FIG. 10 is a perspective view of the fifth embodiment of the cuff for a blood pressure meter.

FIGS. 9 and 10 are a plan view and a perspective view, respectively, of a fifth embodiment of the cuff for a blood pressure meter. This cuff for a blood pressure meter comprises basic structure 1, which is formed from a membrane, and containment walls 2, which are attached to one surface of basic structure 1. On the inner portion of the surface to which the containment walls are attached, fitting (lower cuff) 15 anchors a number of protruding bodies. Belt 1 and fitting 15 are molded together. Locking device (locking tab) 13 is on one end of belt 1 and lock (slit) 14 is on the other end. Locking tab 13 engages with lock 14 so that the belt assumes a cylindrical form. Locking tab 13 becomes narrow near its base to form notches 13a. The width of tab 13 between the notches is substantially equal to the length of slit 14.

Figure 11:
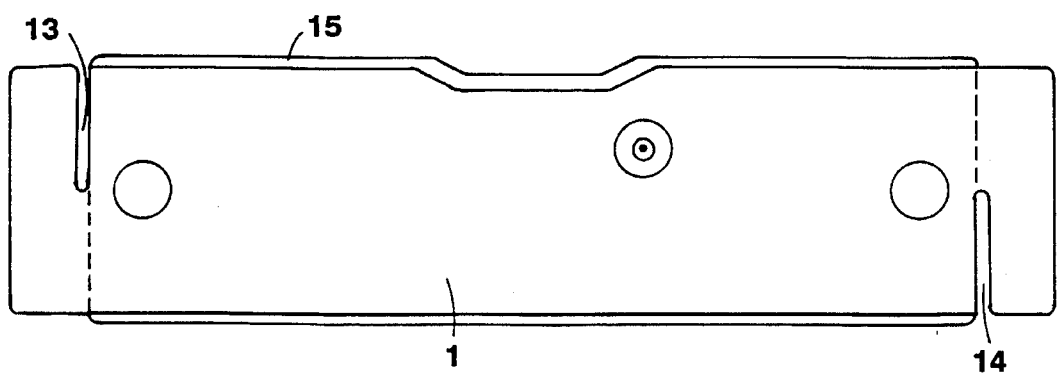
FIG. 11 is a plan view of the fifth embodiment of the cuff for a blood pressure meter.

FIG. 11 is a plan view of the cuff for a blood pressure meter showing a modification of locking device 13 and lock 14. In this embodiment, locking device 13 comprises a notch on the inner surface of one end of structure 1, while the other end of structure 1 has a notch 14 cut into the opposite side so that the two notches can engage with each other.

In a cuff of this embodiment, basic structure 1 is rolled into a cylinder, and locking device 13 is fitted into lock 14. This design makes it quite simple to assemble the cylindrical cuff shown in FIG. 11. Additionally, this cuff can easily be fitted into the actual blood pressure meter.

Figure 12:
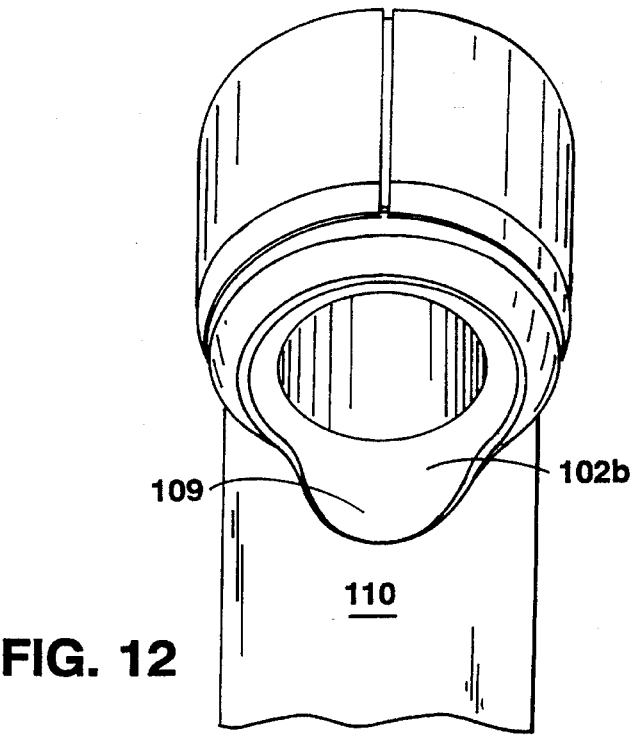
FIG. 12 is a perspective view of a finger bed of a sixth embodiment of the cuff for a blood pressure meter.
Figure 18:
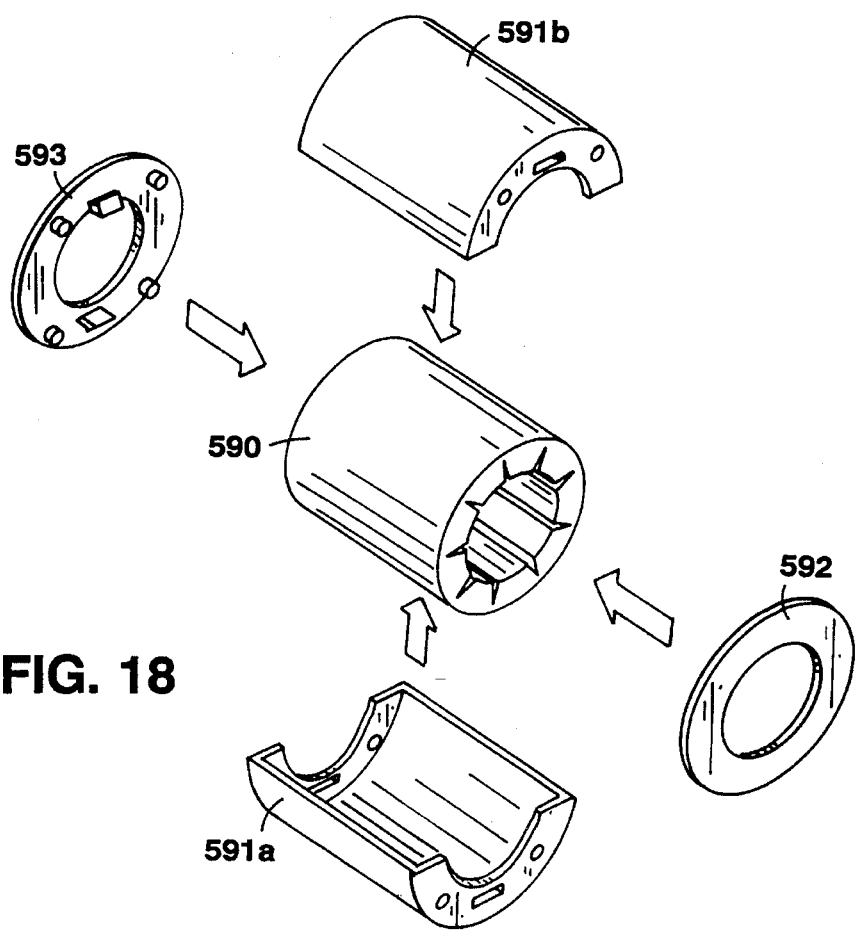
FIG. 18 is an exploded view of a conventional cuff comprising five elements.

FIG. 12 shows a sixth embodiment comprising finger bed 109 on cuff holder segment 102b on which a patient can rest his finger after it has been inserted in the cuff cylinder. This ensures that the patient's finger is relaxed in order to obtain an accurate blood pressure reading.

Figures 13, 14:
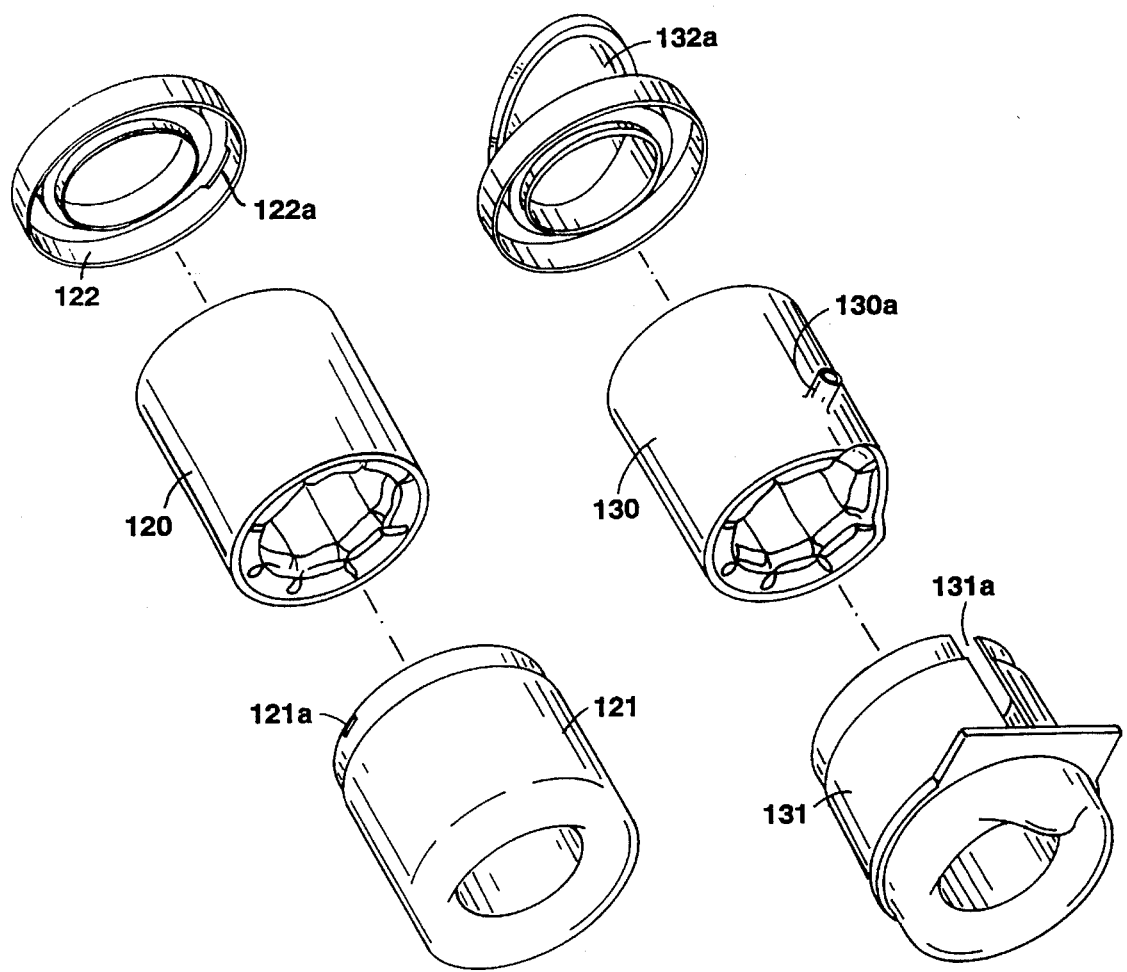
FIG. 13 is a exploded view of a cuff comprising three segments.
FIG. 14 is a exploded view of a cuff with a finger bed comprising three segments.
Figure 15:
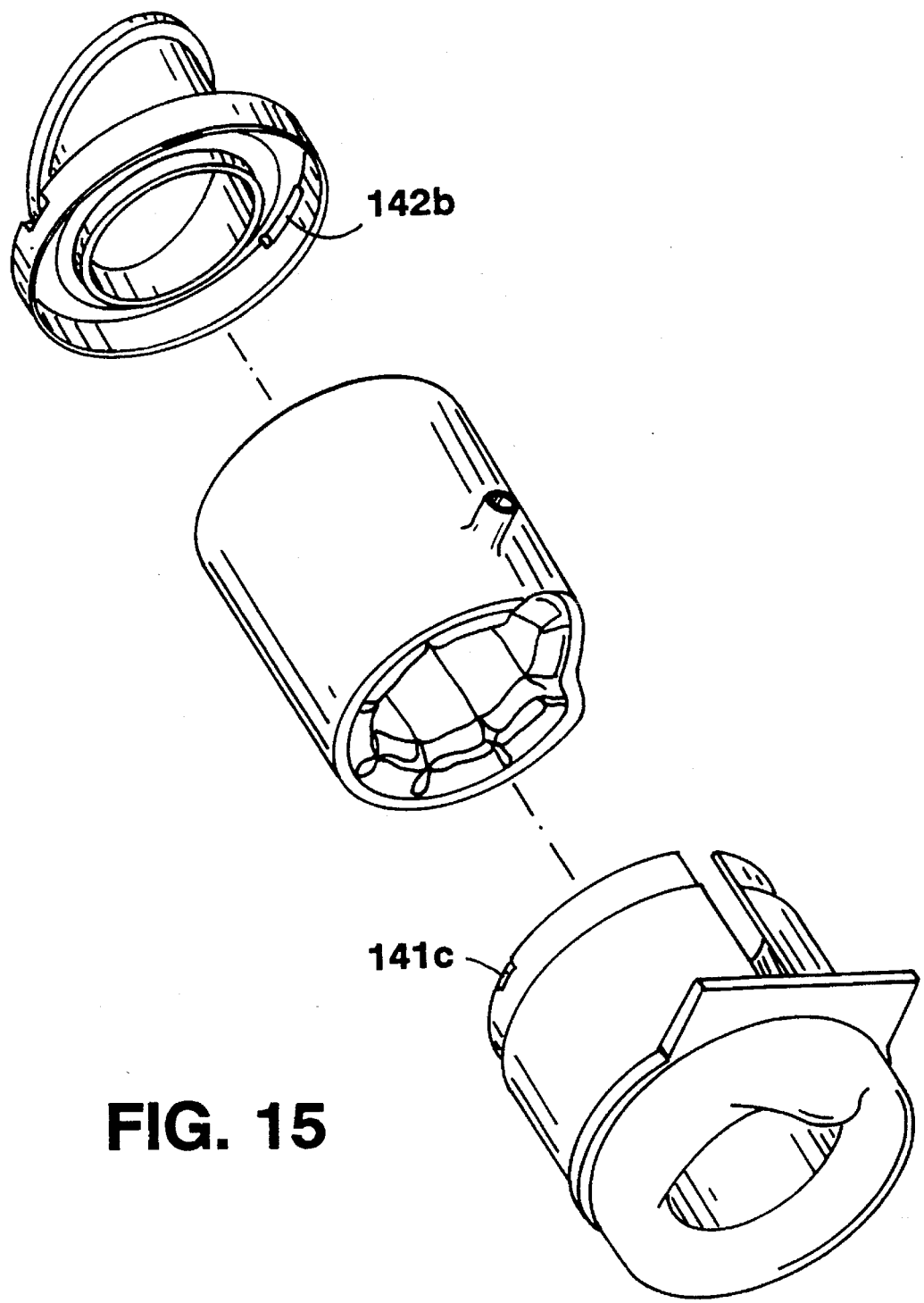
FIG. 15 is an exploded view of a cuff with a finger bed comprising three segments.
Figure 16:
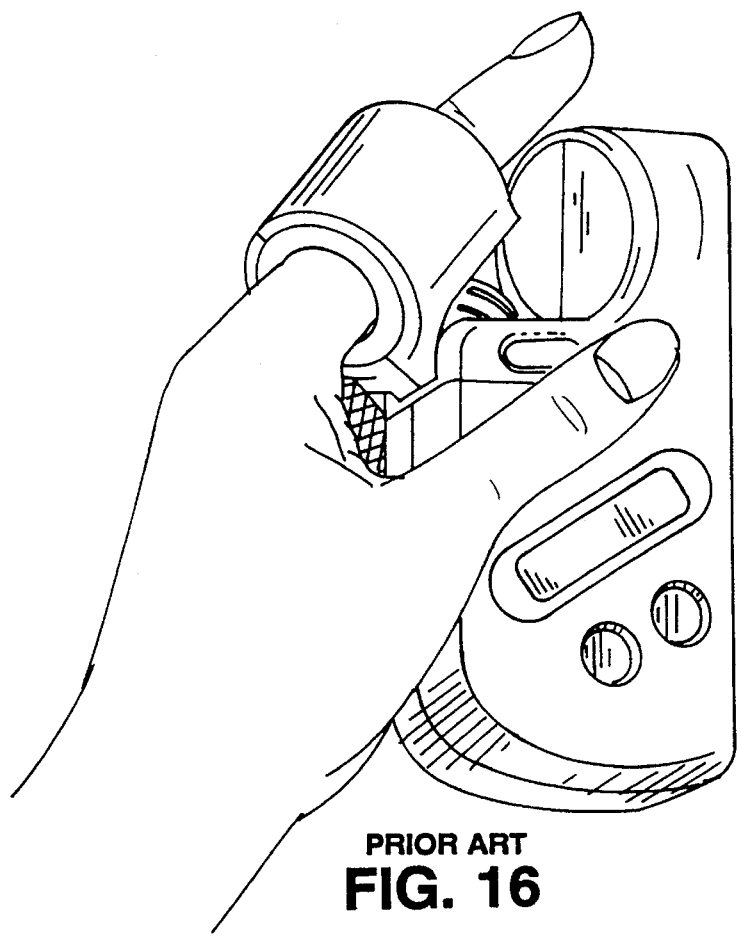
FIG. 16 is a perspective view of a conventional finger cuff blood pressure meter.
Figure 17:
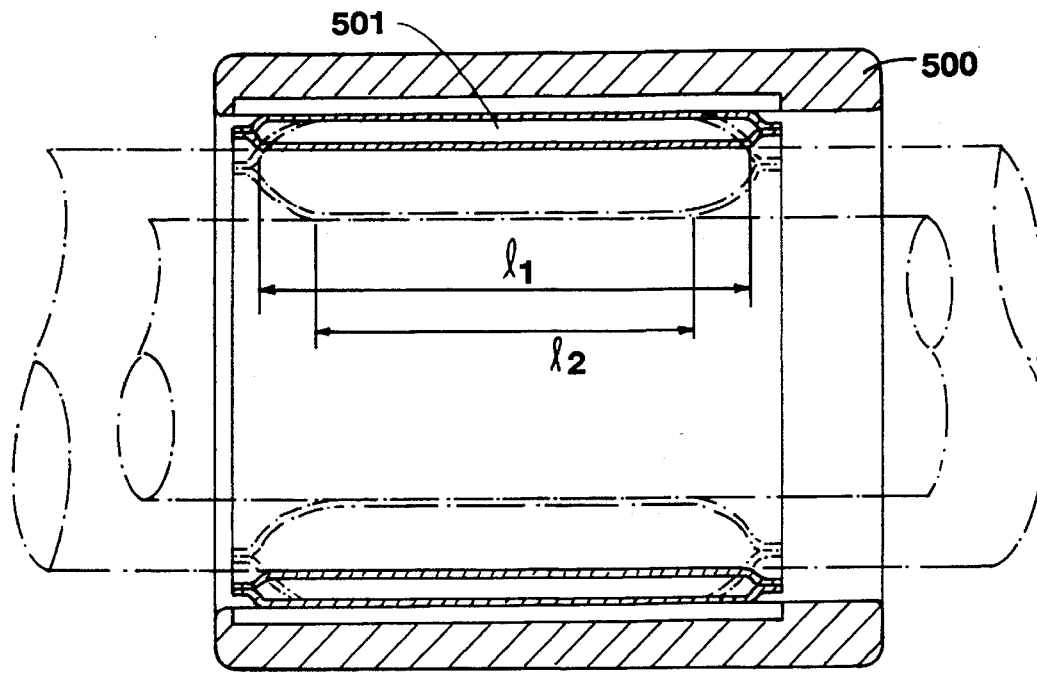
FIG. 17 is a cross-sectional view of a conventional finger cuff for a blood pressure meter.

FIGS. 13–15 show cuffs comprising three segments, cuff main unit, cuff holder, and cuff holder segment. FIG. 13 shows a basic configuration of three segments. The cuff main unit 120 includes basic structure, protruding bodies, and containment wall. When assembling the cuff, cuff main unit 120 is inserted into cuff holder 121 and then attached to cuff holder segment 122. Projection 122a on cuff holder segment 122 engages with the slit 121a on cuff holder 121 in order to assemble the cuff properly. This configuration does not show a finger bed, although one could be provided.

FIG. 14 is another example of a cuff comprising three segments. Cuff main unit 130 has a nozzle 130a. Cuff holder 131 has a slot 131a to insert the nozzle 130a. A stopper 131b on cuff holder 131 is also provided for easy assembling. This configuration also shows a finger bed 132a.

FIG. 15 is a modification of the cuff shown in FIG. 14. This example has projection 142b which engages with slit 141c for easy assembling.

The cuff for a blood pressure meter described in the first through fourth embodiments has folded portions on the walls of the chambers 6 which cause the contacting portions of the containment walls, which contact a patient's finger, to remain parallel with respect to the bottoms of the chambers when those chambers, which are located between the basic structure and the containment walls, are filled with compressed air.

The cuff for a blood pressure meter described in the fifth embodiment has a locking device on one end of its basic structure and a lock to receive the locking device on the other end of the basic structure. Thus, a cylindrical cuff can easily be formed by fitting this locking device into the lock. Such a cuff can easily be fitted into the actual blood pressure meter.

The cuff for a blood pressure meter of the sixth embodiment has a finger bed. The finger bed insures that the finger is relaxed in order to measure the blood pressure accurately.

In the described embodiments cuff for a blood pressure meter of this invention has three segments. This allows for easy assembly and a shorter assembly time.

What is claimed is:

1. A cylindrical cuff for a blood pressure meter, said cylindrical cuff comprising:

a belt having a plurality of protruding bodies disposed on one side of said belt, each of said protruding bodies having a flat surface facing a center of said cylindrical cuffs, each of said flat surfaces representing an innermost surface of said protruding body with respect to the center of said cylindrical cuff; and at least one chamber disposed on said one side of said belt for receiving compressed air and accommodating said protruding bodies therein.

2. A cylindrical cuff for a blood pressure meter as claimed in claim 1, said cuff further comprising:

at least one containment wall disposed on said plurality of protruding bodies which are disposed on said one side of said belt, said containment wall and said belt forming said chamber for receiving compressed air, said containment wall having ends and a surface portion, said surface portion adapted to contact a patient's finger; and at least a pair of folded portions, each of said folded portions disposed at an end of said containment wall, said folded portions causing a surface portion of said containment wall to remain parallel to said flat surfaces of said protruding bodies when said chamber formed by said belt and said containment wall is filled with compressed air.

3. A cylindrical cuff for a blood pressure meter as claimed in claim 2, wherein said folded portions comprise a side fitting segment, an outer curved segment, and an inner curved segment, wherein said outer curved segment starts at an end of said side fitting segment and is folded until it is parallel to said side fitting segment, and said inner curved segment starts at an end of said outer curved segment and is folded until it is parallel to said outer curved segment whereby said folded portions are folded back upon themselves along a line parallel to a path of said flat surfaces of said protruding bodies.

4. A cylindrical cuff for a blood pressure meter as claimed in claim 3, wherein said side fitting segment is thicker than said folded portions, and said outer curved segment and said inner curved segment are the same width as said surface portion of said at least one containment wall.

5. A cylindrical cuff for a blood pressure meter as claimed in claim 2, wherein each of said at least one containment wall further comprises a side fitting segment, said side fitting segment mounting said containment wall to said belt and being thicker than said folded portions.

6. A cylindrical cuff for a blood pressure meter as claimed in claim 2, wherein said belt is a membrane and has two ends, said belt having a locking device disposed on one end and a lock disposed on said other end, said belt and said at least one containment wall are molded together, and said locking device engages with said lock whereby said belt assumes a cylindrical form.

7. A cylindrical cuff for a blood pressure meter as claimed in claim 6, wherein said locking device is a tab and said lock is a slit.

8. A cylindrical cuff for a blood pressure meter as claimed in claim 6, wherein said locking device and said lock are notches.

9. A cylindrical cuff for a blood pressure meter as claimed in claim 2, said cuff further comprising at least one folding guard extending from said folded portion and disposed over an end of said containment wall.

10. A cylindrical cuff for blood pressure meter as claimed in claim 9, wherein said folding guard is disposed over said side fitting segment.

11. A cylindrical cuff for a blood pressure meter as claimed in claim 2, said cuff further comprising:

a cuff main unit;

a cuff holder having a slit; and a cuff holder segment having a projection, wherein said cuff main unit is inserted into said cuff holder, and said slit of said cuff holder engages said projection of said cuff holder segment such that said cuff holder and said cuff holder segment are attached whereby said cuff is assembled.

12. A cylindrical cuff for a blood pressure meter as claimed in claim 2, said cuff further comprising:

a cuff main unit having a nozzle;

a cuff holder having a slot and a stopper; and a cuff holder segment, wherein said nozzle of said cuff main unit engages said slot of said cuff holder, and wherein said cuff holder has a slit, and said cuff holder segment has a projection, whereby said slit of said cuff holder engages with said projection of said cuff holder segment to assemble said cuff.

13. A cylindrical cuff for a blood pressure meter as claimed in claim 1, said cuff further comprising means for supporting a patient's finger.

14. A cylindrical cuff for a blood pressure meter as claimed in claim 13, wherein said means for supporting a patient's finger comprises a finger bed.

15. A cylindrical cuff for a blood pressure meter as claimed in claim 13, wherein said means for supporting a patient's finger extends from an outside edge of said belt.

* * * * *

UNITED STATES PATENT AND TRADEMARK OFFICE
CERTIFICATE OF CORRECTION

PATENT NO. : 5,511,551
DATED      : April 30, 1996
INVENTOR(S): Yoshihiko SANO et al.

It is certified that error appears in the above-indentified patent and that said Letters Patent is hereby corrected as shown below:

On the title page, insert item
[30]          Foreign Application Priority Data

March 15, 1993     [JP]     Japan . . . . . . . . . 5-53638
November 16, 1993  [JP]     Japan . . . . . . . . . 5-20670

Signed and Sealed this

Twentieth Day of August, 1996

Attest:

BRUCE LEHMAN

*Attesting Officer*      *Commissioner of Patents and Trademarks*